United States Patent
Acharya et al.

(10) Patent No.: US 10,872,387 B2
(45) Date of Patent: Dec. 22, 2020

(54) HOSPITAL BED EVENT NOTIFICATION

(71) Applicant: TeleTracking Technologies, Inc., Pittsburgh, PA (US)

(72) Inventors: Arpan Acharya, McDonald, PA (US); Harold Barrett, Greensburg, PA (US); Don DeCorte, Pittsburgh, PA (US); Tom Perry, Dubois, PA (US)

(73) Assignee: TeleTracking Technologies, Inc., Pittsburgh, PA (US)

(*) Notice: Subject to any disclaimer, the term of this patent is extended or adjusted under 35 U.S.C. 154(b) by 18 days.

(21) Appl. No.: 13/840,212

(22) Filed: Mar. 15, 2013

(65) Prior Publication Data
US 2019/0188812 A1    Jun. 20, 2019

(51) Int. Cl.
*G06Q 50/22* (2018.01)
*G16H 40/20* (2018.01)
*G06Q 10/08* (2012.01)

(52) U.S. Cl.
CPC ............ *G06Q 50/22* (2013.01); *G06Q 10/08* (2013.01); *G16H 40/20* (2018.01)

(58) Field of Classification Search
CPC ........ G06Q 50/22; G06Q 50/24; G06Q 10/10; G06F 19/327; G06F 19/322; G06F 19/3418; G08B 21/22; G16H 40/20
USPC .......................................................... 705/2
See application file for complete search history.

(56) References Cited

U.S. PATENT DOCUMENTS

| | | | |
|---|---|---|---|
| 2003/0073434 A1 | 4/2003 | Shostak | |
| 2007/0080801 A1* | 4/2007 | Weismiller | A61B 5/411 340/539.13 |
| 2007/0192133 A1* | 8/2007 | Morgan | G06F 19/321 705/2 |
| 2008/0126126 A1* | 5/2008 | Ballai | 705/2 |
| 2008/0312975 A2* | 12/2008 | Rosow | G06Q 10/02 705/5 |
| 2010/0007498 A1 | 1/2010 | Jackson | |
| 2011/0070833 A1 | 3/2011 | Perkins et al. | |
| 2011/0208541 A1* | 8/2011 | Wilson | A61G 7/018 705/3 |

FOREIGN PATENT DOCUMENTS

| | | |
|---|---|---|
| EP | 1914650 A2 | 4/2008 |
| GB | 2467631 A | 8/2010 |
| WO | 2007047045 A1 | 4/2007 |

OTHER PUBLICATIONS

European Search Report for Application No. EP14160253, dated Jul. 9, 2014, 3 pages, Munich, Germany.
(Continued)

*Primary Examiner* — Hiep V Nguyen
(74) *Attorney, Agent, or Firm* — Ference & Associates LLC

(57) ABSTRACT

An aspect provides a method, including receiving an indication that a tag associated with a real time location system has been detected at a pre-determined location, the detected tag being associated with a patient in a hospital; and assigning a status of the patient based on detection of the tag; and updating a bed availability indication based on detection of the tag. Other aspects are described and claimed.

14 Claims, 4 Drawing Sheets

(56) References Cited

OTHER PUBLICATIONS

Statement in Accordance With the Notice From the European Patent Office Dated October 1, 2007 Concerning Business Methods (OJ EPO Nov. 2007), Nov. 1, 2007, XP002456252, 1 page, Munich, Germany.
Notice From the European Patent Office dated Oct. 1, 2007 Concerning Business Methods (Official Journal EPO Nov. 2007), Nov. 1, 2007, XP007905525, pp. 592-593, Munich, Germany.

* cited by examiner

HOSPITAL BED EVENT NOTIFICATION

BACKGROUND

Hospitals are under increasing pressure to reduce the duration of a hospital stay. Thus, it is in a hospital's interest to ensure that when one patient is discharged from the hospital that the former patient's now unoccupied bed is available for a new patient as quickly as possible.

When a patient's bed becomes unoccupied, various tasks have to be completed before the bed may be occupied by another patient. For example, a hospital's Environmental Services department needs to be notified to service the bed, i.e., the bed needs to be stripped, clean linens placed thereon, etc., and generally readied for a new patient. Once the bed has been serviced, other hospital departments (including the Bed Control department) need to be notified that the bed is ready to be occupied by a new patient.

Similarly, when a hospital bed has been occupied by a patient, the Bed Control department needs to be notified that the bed is not available to be occupied by a new patient.

BRIEF SUMMARY

In summary, one aspect provides a method, comprising receiving an indication that a tag associated with a real-time location system has been detected at a pre-determined location; the detected tag being associated with a patient in a hospital; assigning a status of the patient based on detection of the tag; and updating a bed availability indication based on detection of the tag.

Another aspect provides an information handling device, comprising: a memory operatively coupled to the one or more processors that stores instructions executable by the one or more processors to perform acts comprising: receiving an indication that a tag associated with a real time location system has been detected at a pre-determined location, the detected tag being associated with a patient in a hospital; and assigning a status of the patient based on detection of the tag; and updating a bed availability indication based on detection of the tag.

A further aspect provides a program product, comprising: a storage medium having computer program code embodied therewith, the computer program code comprising: computer program code configured to receive an indication that a tag associated with a real time location system has been detected at a pre-determined location, the detected tag being associated with a patient in a hospital; and computer program code configured to assign a status of the patient based on detection of the tag; and updating a bed availability indication based on detection of the tag.

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in conjunction with the accompanying drawings. The scope of the invention will be pointed out in the appended claims.

DETAILED DESCRIPTION

Figure 1:
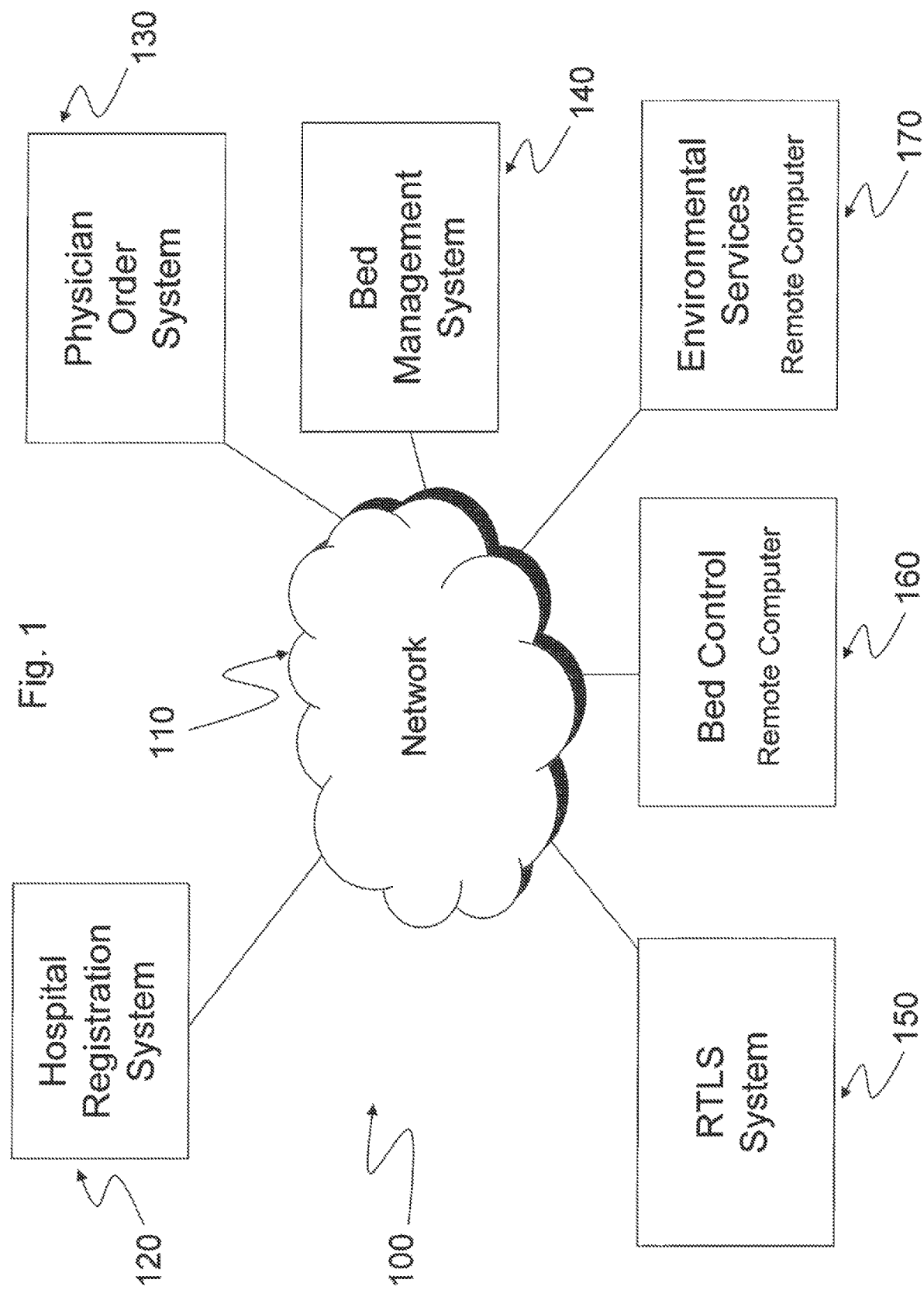
FIG. 1 illustrates various systems and remote computers which may be connected to a hospital information network.

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well known structures, materials, or operations are not shown or described in detail to avoid obfuscation.

Hospitals use various systems including an internal registration system such as an Admissions Discharge Transfer (ADT) system and various third party systems to manage bed inventory. ADT systems, however, generally require manual input and are not updated in real-time and, for example, data may be updated several hours after a patient has left the hospital. Third party systems similarly require manual input, which may or may not be done consistently in real time. Moreover, manual inputs are required to match discharge status with bed availability states.

Accordingly, an embodiment provides a mechanism by which appropriate hospital personnel may be notified in a timely manner of a bed event by automating bed availability with patient status. A patient may be outfitted with an active or passive identification tag as part of a Real-Time Location System (RTLS) used to automatically track and identify the location of the patient within the hospital. The RTLS system may cover the entire hospital, a portion of the hospital (i.e., nursing areas, surgical suites, etc.), or the discharge areas of the hospital, depending on the preferences of the hospital administration. Any suitable RTLS technology may be used, including radio frequency, optical (i.e., infrared), and acoustic (i.e., ultrasound). Dual mode and single mode systems may also be used. (An example of a dual mode system is an identification tag that receives a signal from an infrared beacon and broadcasts an RF signal. The RF signal includes an identifier associated with the beacon from which the infrared signal was received together with an identifier associated with the tag itself) A patient's identification tag may be a radio frequency identification (RFID) tag, an infrared identification tag, or a sound identification tag, or any suitable identification tag. Such tags may be placed within a standard badge, worn with standard hospital ID bands, or located in any suitable place.

In one embodiment, recovery boxes are strategically placed throughout the hospital facility and when a patient leaves the designated area (the hospital itself, a surgical suite, etc.) the tag is removed from the patient by hospital personnel and placed in the recovery box. The placement of the tag within the recovery box, together with location of the recovery box, would then function to identify the patient associated with the tag as having experienced an unoccupied bed event.

In another embodiment, appropriate sensors are strategically placed through the hospital facility and when a patient leaves the designated area (the hospital itself, a surgical suite, etc.) hospital records are automatically reviewed to determine if there is a precursor to an unoccupied bed event therein for the patient associated with the tag (i.e., a discharge order). If so, the patient's bed is identified as having experienced an unoccupied bed event.

The illustrated example embodiments will be best understood by reference to the figures. The following description is intended only by way of example, and simply illustrates certain example embodiments.

Referring to FIG. 1, a system 100 in an embodiment is shown. Network 110 operative connects a number of components, including Hospital Registration System 120, Physician Order System 130, Bed Management System 140, and Real-Time Location System (RTLS) 150. A hospital typically provides the Hospital Registration System 120 and Physician Order System 130. A vendor typically provides Bed Management System 140, and Real-Time Location System (RTLS) 150.

A Bed Management System 140 will typically have data available to it from the Hospital Registration System 120 and the Physician Order System 130 using the Hospital Level 7 (HL7) protocol. Bed Management System 140 may also make available status update messages to Physician Order System 130. An example of a Bed Management System 140 is the Bed Management Suite from TeleTracking Technologies, Inc., of Pittsburgh, Pa. A suitable RTLS System 150 may be obtained from CenTrak, Inc., of Newtown, Pa. Remote computers in Bed Control 160 and Environmental Services 170 may be used by hospital staff to access various information, including information from Bed Management System 140 relating to bed status (i.e., bed occupied, bed unoccupied, or bed needing service).

Figure 2:
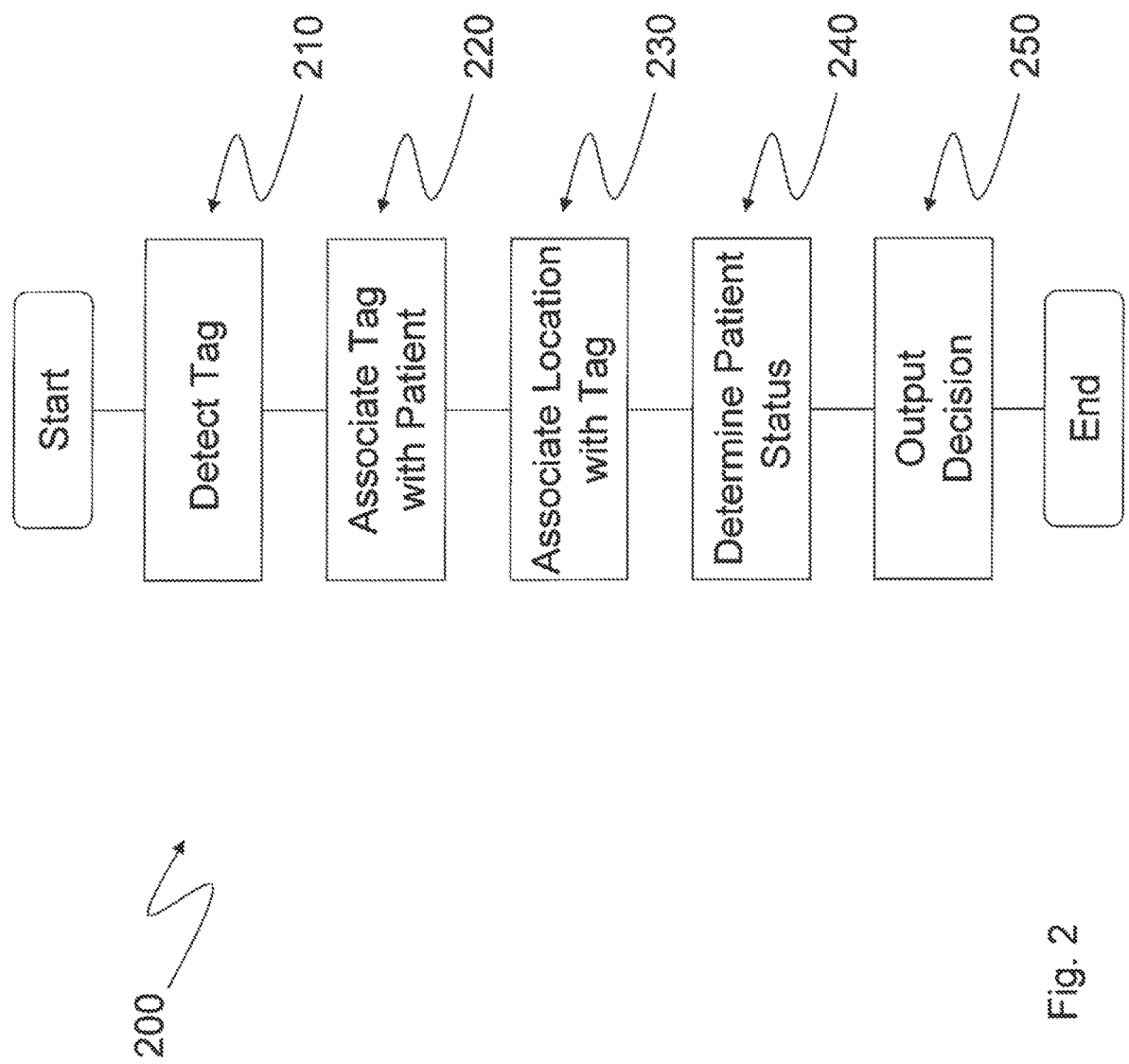
FIG. 2 illustrates a flow chart in accordance with an embodiment.

Referring now to FIG. 2, a flow chart 200 is shown illustrating an embodiment. At Step 210, a tag is detected by RTLS 150. At Step 220, the tag is associated with a patient, preferably by Bed Management System 140. This association would be made by using information inputted into Bed Management System 140 when a patient came into the hospital (i.e., updating a patient's record to include information on the RTLS tag given to the patient). Such information may either be inputted directly into Bed Management System 140, inputted into Hospital Registration System 120 and then pushed to Bed Management System 140, or made available in any suitable manner. At Step 230, the tag is associated with a location. This would be done, for example, by noting the location of the RTLS sensor within the RTLS system 150 which detected the tag. At Step 240, the patient status is determined (i.e., does the patient status indicate a bed unoccupied event). As discussed below, this may be done by determining if a discharge order for the patient has been entered into Physician Orders System 130. At Step 250 a decision is outputted on whether or not to indicate a bed unoccupied event has occurred. If it is determined that a bed unoccupied event has occurred, Bed Management System 140 would then update the status of the bed associated with the patient and make any required notifications to hospital staff.

Such notifications may include notifying the hospital's Environmental Services Department to service the bed, and once servicing has been completed, notifying the hospital's Bed Control department the bed is now ready to be occupied by a patient. Such notifications would typically occur through Bed Management System 140. As shown in FIG. 1, Bed Control Remote Computer 160 and Environmental Services Remote Computer 170 may be used by the Bed Control and Environmental Services Departments to access information from Bed Management System 140. Alternatively, Bed Management System 140 may push information directly to the relevant hospital staff (i.e., directly notify cleaning personnel).

Embodiments may be implemented in a variety of scenarios, which will now be discussed.

Discharge Drop Box

In this embodiment, a clinician (which could be a nurse, transporter, or other clinician) removes the RTLS tag from a patient and places the tag into a Discharge Drop Box, which is placed at an appropriate location such as the exit of a surgical suite within the hospital or at an exit of the hospital itself. The discharge drop box preferably has an RTLS sensor to recognize a tag being present in the box (but not outside the box). The information conveyed includes both the tag is within a discharge drop box and the location of the discharge drop box. This embodiment may be implemented using any appropriate RTLS technology (i.e., passive, active, infrared, sound, etc.) where the tag is detected in the discharge drop box, but not outside of the box. After determining that the tag is located within the drop box, an embodiment updates a bed availability status of the bed within the system, e.g., indicates that this patient's bed is no longer occupied and is in need of service. An embodiment may use other information in making this determination, e.g., a discharge order for the patient is also available.

Discharge Location

In this embodiment, a patient with an RTLS tag is detected via RTLS in a location designated as a "discharge location". A "discharge location" may be any appropriate location, such as the exit of a suite within the hospital or at an exit of the hospital itself. When the patient is detected in a discharge location and the patient is identified, it is determined if the patient has a discharge appropriate status (i.e., there is a precursor to discharge event), typically by determining if Physician Order System (130) indicates that there is a discharge order for the patient. If the patient does not have discharge appropriate status, even though the patient is detected in the discharge location, the patient will not be treated as having been discharged and the bed availability status will not be updated. This embodiment is appropriate for passive tag technology (i.e., RFID), as well as active, dual mode technology. If the patient does have a discharge appropriate status, the bed availability status is updated.

Admit/Transfer

RTLS technology may also be used through out a hospital, not just at the boundaries of the hospital (or hospital department, i.e., a surgical suite). In such a circumstance, when a patient with an RTLS tag is detected in a location typically associated with a patient bed (i.e., a nursing unit and not an operating room), and the location is the same as the pre-assigned bed for that patient, it is preferred that the Bed Management System 140 indicate that the bed is occupied. If there is no pre-assigned bed for the patient, or if a bed different than the pre-assigned bed is detected, the bed will generally not be treated as being occupied.

Whether a patient is being admitted or transferred may be determined by whether the patient does or does not have a location typically associated with a patient bed. If the patient does not have a location typically associated with a patient bed, the patient is preferably treated as being admitted. If the patient does have a location typically associated with a patient bed, the patient is preferably treated as being transferred. Bed Management System 140 may be configured to determine, based on the time a patient is in a location, to indicate a bed is occupied. For example, if a patient with an RTLS tag is detected in a location typically associated with a patient bed and the patient has been in that location greater than the threshold time (which may vary for an admission or transfer), then if the bed is not occupied by another patient, the Bed Management System 140 may treat the bed as occupied by the patient with the detected RTLS tag. If Bed Management System 140 indicates the bed is occupied by another patient (it is not necessary for the occupying patient to have an RTLS tag), Bed Management System 140 will not treat the bed as being occupied by the patient wearing the detected RTLS tag. Bed Management System 140 preferably implements this treatment even if the patient wearing the detected RTLS tag has a different pre-assigned bed.

Figure 3:
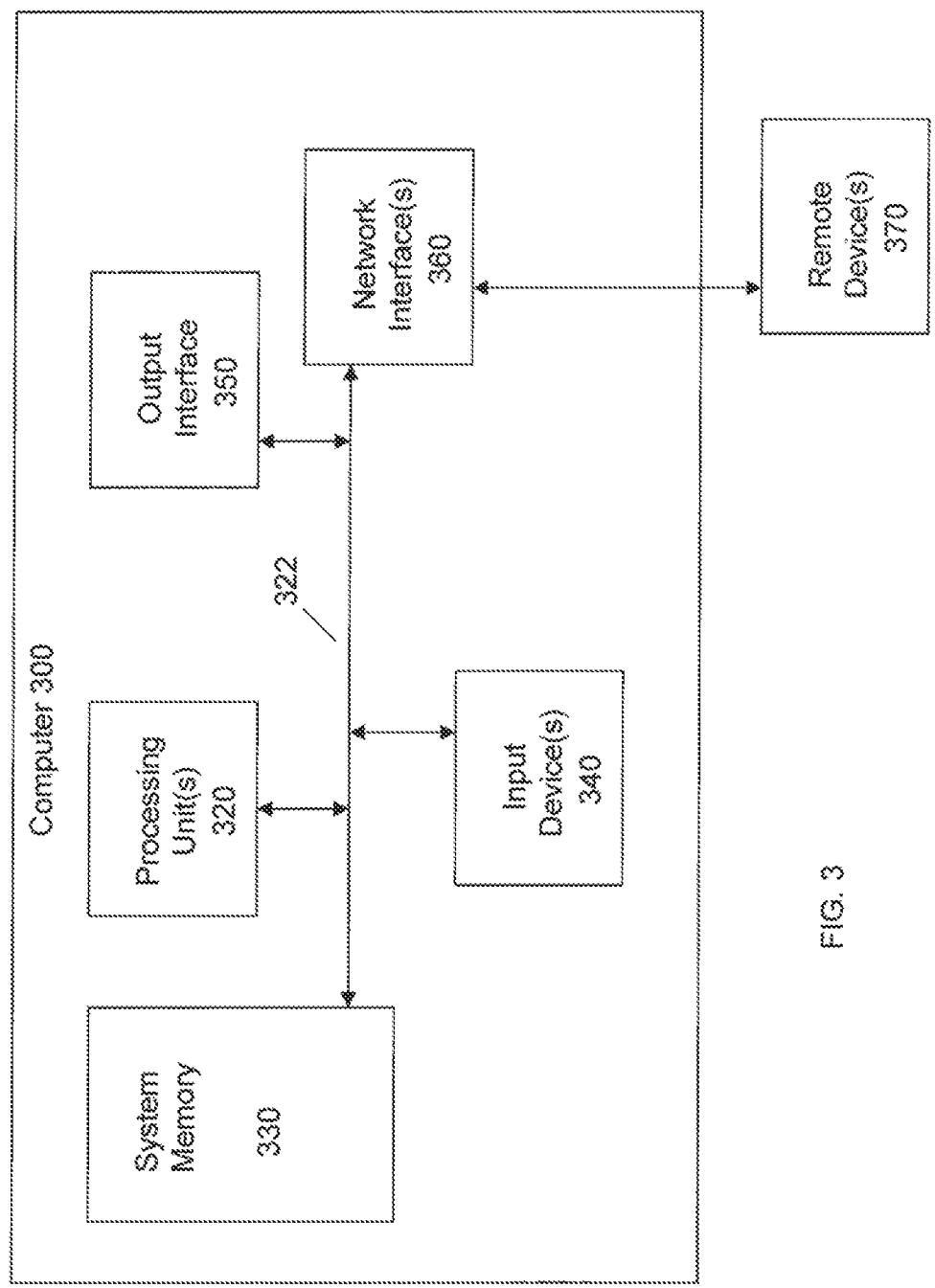
FIG. 3 illustrates an example information handling device and components thereof.

Referring now to FIG. 3, an example device that may be used in implementing one or more embodiments includes a computing device in the form of a computer 300. This example device may be a server used in one of the systems in hospital network, or one of the remote computers connected to the hospital network. Components of computer 300 may include, but are not limited to, a processing unit 320, a system memory 330, and a system bus 322 that couples various system components including the system memory 330 to the processing unit 320. Computer 300 may include or have access to a variety of computer readable media, including databases. The system memory 330 may include non-signal computer readable storage media, for example in the form of volatile and/or nonvolatile memory such as read only memory (ROM) and/or random access memory (RAM). By way of example, and not limitation, system memory 330 may also include an operating system, application programs, other program modules, and program data.

A user can interface with (for example, enter commands and information) the computer 300 through input devices 340. A monitor or other type of device can also be connected to the system bus 322 via an interface, such as an output interface 350. In addition to a monitor, computers may also include other peripheral output devices. The computer 300 may operate in a networked or distributed environment using logical connections to one or more other remote device(s) 370 such as other computers. The logical connections may include network interface(s) 360 to a network, such as a local area network (LAN), a wide area network (WAN), and/or a global computer network, but may also include other networks/buses.

Figure 4:
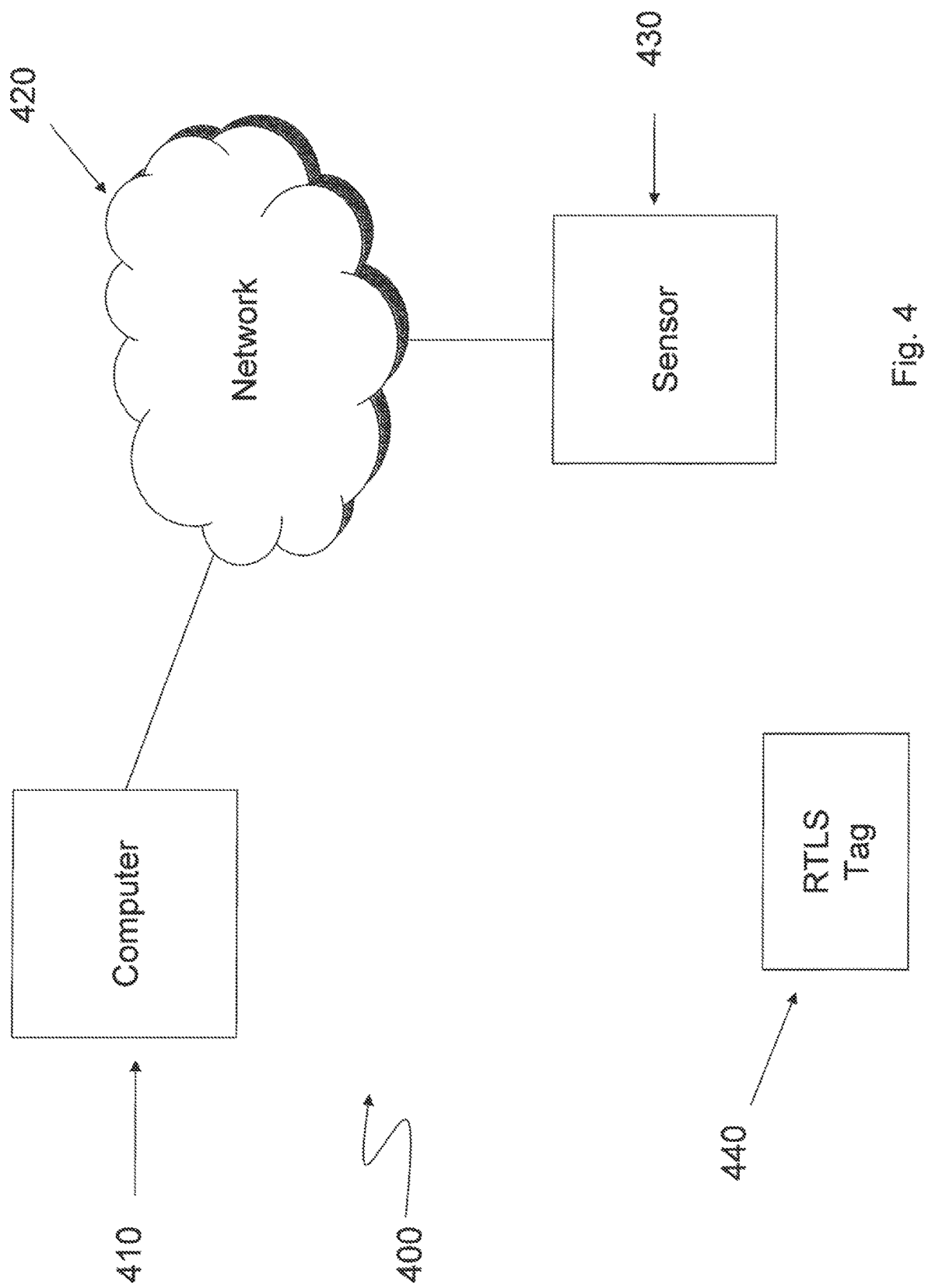
FIG. 4 illustrates the components of an example RTLS system.

Referring now to FIG. 4, the general components of a Real-Time Location System 400 are illustrated. The components include computer 410 and sensor 430, which are connected via network 420 (other suitable connections may also be used), and RTLS tag 440.

As will be appreciated by one skilled in the art, various aspects may be embodied as a system, method or device program product. Accordingly, aspects may take the form of an entirely hardware embodiment or an embodiment including software that may all generally be referred to herein as a "circuit," "module" or "system." Furthermore, aspects may take the form of a device program product embodied in one or more device readable medium(s) having device readable program code embodied therewith.

Any combination of one or more non-signal device readable medium(s) may be utilized. The non-signal medium may be a storage medium. A storage medium may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing.

Program code embodied on a storage medium may be transmitted using any appropriate medium, including but not limited to wireless, wireline, optical fiber cable, RF, et cetera, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of connection or network, including a local area network (LAN) or a wide area network (WAN), or the connection may be made through other devices (for example, through the Internet using an Internet Service Provider) or through a hard wire connection, such as over a USB connection.

Aspects are described herein with reference to the figures, which illustrate example methods, devices and program products according to various example embodiments. It will be understood that the actions and functionality illustrated may be implemented at least in part by program instructions. These program instructions may be provided to a processor of a general purpose information handling device, a special purpose information handling device, or other programmable data processing device or information handling device to produce a machine, such that the instructions, which execute via a processor of the device implement the functions/acts specified.

The program instructions may also be stored in a device readable medium that can direct a device to function in a particular manner, such that the instructions stored in the device readable medium produce an article of manufacture including instructions which implement the functions/acts specified.

The program instructions may also be loaded onto a device to cause a series of operational steps to be performed on the device to produce a device implemented process such that the instructions which execute on the device provide processes for implementing the functions/acts specified.

This disclosure has been presented for purposes of illustration and description but is not intended to be exhaustive or limiting. Many modifications and variations will be apparent to those of ordinary skill in the art. The example embodiments were chosen and described in order to explain principles and practical application, and to enable others of ordinary skill in the art to understand the disclosure for various embodiments with various modifications as are suited to the particular use contemplated.

Thus, although illustrative example embodiments have been described herein with reference to the accompanying figures, it is to be understood that this description is not limiting and that various other changes and modifications may be affected therein by one skilled in the art without departing from the scope or spirit of the disclosure.

What is claimed is:

1. A method, comprising:

receiving, at a bed management system, an indication that a tag associated with a real time location system and assigned to and worn by a patient in a hospital has been detected at a predetermined location within the hospital having a patient bed, wherein the predetermined location and corresponding patient bed are associated within the real time location system, wherein the indication is received in response to a sensor within the predetermined location detecting the tag worn by the patient at the predetermined location;

automatically updating, responsive to determining that the predetermined location is associated with a patient bed that was previously assigned to the patient and on a display screen associated with the bed management system, a status of the patient bed associated with the predetermined location from an unoccupied status to an occupied status assigned to the patient in the bed management system, wherein the status of the patient bed within the bed management system is not changed if the patient bed is not previously assigned to the patient and the patient is at the predetermined location, corresponding to the location of the patient bed, less than a predetermined threshold of time;

automatically, responsive to detecting the tag at the predetermined location having a patient bed, updating a patient status within the real time location tracking system, wherein the updating the patient status comprises updating the patient status to admitted if the patient did not have a previously assigned patient bed, wherein the updating the patient status comprises updating the patient status to transferred if the patient had a previously assigned patient bed not corresponding to the patient bed of the predetermined location;

receiving, at the bed management system, an indication that the tag worn by the patient assigned to the patient bed having an occupied status has been detected at a pre-determined discharge location;

automatically assigning, through the bed management system, a discharged status to the patient based on detection of the tag in the pre-determined discharge location;

automatically updating, on the display screen associated with the bed management system, a status of the patient bed associated with the patient in the bed management system based on detection of the tag in the pre-determined discharge location and based upon the discharged status of the patient, wherein the updating comprises changing and displaying, on the display screen associated with the bed management system, the status indication of the bed from the occupied status to a status of bed needing service; and automatically sending, by the bed management system, a notification of the changed bed availability to hospital staff.

2. The method of claim 1, further comprising determining a precursor event comprising determining that a discharge order exists for the patient;

wherein the updating proceeds if the system contains a discharge order for the patient.

3. The method of claim 1, wherein the bed management system comprises a system that displays a comprehensive view of bed statuses for each unit within a hospital.

4. The method of claim 1, wherein the sensor that recognizes the detected tag is selected from the group consisting of: an infrared beacon that transmits an infrared signal to the detected tag, a radio frequency sensor, ultrasound sensor, infrared sensor, ultrasound transmitter, and ultrasound transducer.

5. The method of claim 1, wherein the status of bed needing service comprises an indication selected from the group consisting of: the bed needs cleaned, the bed is dirty, and the bed is unoccupied.

6. The method of claim 1, further comprising automatically updating, on a display screen associated with the bed management system, a status of the bed associated with the discharged patient in the bed management system responsive to determining the bed has been serviced, wherein the updating comprises changing and displaying, on the display screen associated with the bed management system, the availability indication of the bed from the bed needing service status to a status of unoccupied.

7. The method of claim 1, wherein the receiving an indication comprises receiving an indication from a sensor located within a discharge drop box that the tag worn by the patient has been detected within the discharge drop box.

8. The method of claim 1, wherein the automatically assigning is responsive to determining a discharge order exists for the patient; and wherein the automatically assigning comprises not changing the status of the patient based upon detection of the tag in the pre-determined discharge location if a discharge order does not exist for the patient.

9. The method of claim 1, comprising automatically updating, responsive to determining that the predetermined location is not associated with a patient bed, a status of the patient to admitted.

10. An information handling device, comprising:

a memory operatively coupled to one or more processors that stores instructions executable by the one or more processors to perform acts comprising:

receiving, at a bed management system, an indication that a tag associated with a real time location system and assigned to and worn by a patient in a hospital has been detected at a predetermined location within the hospital having a patient bed, wherein the predetermined location and corresponding patient bed are associated within the real time location system, wherein the indication is received in response to a sensor within the predetermined location detecting the tag worn by the patient at the predetermined location;

automatically updating, responsive to determining that the predetermined location is associated with a patient bed that was previously assigned to the patient and on a display screen associated with the bed management system, a status of the patient bed associated with the predetermined location from an unoccupied status to an occupied status assigned to the patient in the bed management system, wherein the status of the patient bed within the bed management system is not changed if the patient bed is not previously assigned to the patient and the patient is at the predetermined location, corresponding to the location of the patient bed, less than a predetermined threshold of time;

automatically, responsive to detecting the tag at the pre-determined location having a patient bed, updating a patient status within the real time location tracking system, wherein the updating the patient status comprises updating the patient status to admitted if the patient did not have a previously assigned patient bed, wherein the updating the patient status comprises updating the patient status to transferred if the patient had a previously assigned patient bed not corresponding to the patient bed of the predetermined location;

receiving, at the bed management system, an indication that the tag worn by the patient assigned to the patient bed having an occupied has been detected at a pre-determined discharge location;

automatically assigning, through the bed management system, a discharged status to the patient based on detection of the tag in the pre-determined discharge location;

automatically updating, on the display screen associated with the bed management system, a status of the patient bed associated with the patient in the bed management system based on detection of the tag in the pre-determined discharge location and based upon the discharged status of the patient, wherein the updating comprises changing and displaying, on the display screen associated with the bed management system, the status indication of the bed from the occupied status to a status of bed needing service; and automatically sending, by the bed management system, a notification of the changed bed availability to hospital staff.

11. The information handling device of claim 10, further comprising determining a precursor event comprising determining that a discharge order exists for the patient;

wherein the updating proceeds if the system contains a discharge order for the patient.

12. The information handling device of claim 10, further comprising automatically updating, on a display screen associated with the bed management system, a status of the bed associated with the discharged patient in the bed management system responsive to determining the bed has been serviced, wherein the updating comprises changing and displaying, on the display screen associated with the bed management system, the availability indication of the bed from the bed needing service status to a status of unoccupied.

13. A program product, comprising:

a non-transitory storage device having computer program code embodied therewith, the computer program code being executable by a processor and comprising:

computer program code configured to receive, at a bed management system, an indication that a tag associated with a real time location system and assigned to and worn by a patient in a hospital has been detected at a predetermined location within the hospital having a patient bed, wherein the predetermined location and corresponding patient bed are associated within the real time location system, wherein the indication is received in response to a sensor within the predetermined location detecting the tag worn by the patient at the predetermined location;

computer program code configured to automatically update, responsive to determining that the predetermined location is associated with a patient bed that was previously assigned to the patient and on a display screen associated with the bed management system, a status of the patient bed associated with the predetermined location from an unoccupied status to an occupied status assigned to the patient in the bed management system, wherein the status of the patient bed within the bed management system is not changed if the patient bed is not previously assigned to the patient and the patient is at the predetermined location, corresponding to the location of the patient bed, less than a predetermined threshold of time;

computer program code configured to automatically, responsive to detecting the tag at the predetermined location having a patient bed, updating a patient status within the real time location tracking system, wherein the updating the patient status comprises updating the patient status to admitted if the patient did not have a previously assigned patient bed, wherein the updating the patient status comprises updating the patient status to transferred if the patient had a previously assigned patient bed not corresponding to the patient bed of the predetermined location;

computer program code configured to receive, at the bed management system, an indication that the tag associated with the patient assigned to the patient bed having an occupied status has been detected at a pre-determined discharge location;

computer program code configured to automatically assign, through the bed management system, a discharged status to the patient based on detection of the tag in the pre-determined discharge location;

computer readable program code configured to automatically update, on the display screen associated with the bed management system, a status of the patient bed associated with the patient in the bed management system based on detection of the tag in the pre-determined discharge location and based upon the discharged status of the patient, wherein to update comprises changing and displaying, on the display screen associated with the bed management system, the status indication of the bed from the occupied status to a status of bed needing service; and computer readable program code configured to automatically send, by the bed management system, a notification of the changed bed availability to hospital staff.

14. The program product of claim 13, further comprising computer readable program code configured to automatically update, on a display screen associated with the bed management system, a status of the bed associated with the discharged patient in the bed management system responsive to determining the bed has been serviced, wherein the updating comprises changing and displaying, on the display screen associated with the bed management system, the availability indication of the bed from the bed needing service status to a status of unoccupied.

* * * * *